(12) United States Patent
Sharkey et al.

(10) Patent No.: US 6,464,727 B1
(45) Date of Patent: Oct. 15, 2002

(54) INTERVERTEBRAL SPACER IMPLANT

(75) Inventors: Hugh R. Sharkey, 830 Partridge Ave., Menlo Park, CA (US) 94025; Henry Fletcher, Cameron Park, CA (US)

(73) Assignee: Hugh R. Sharkey, Redwood City, CA (US)

( * ) Notice: Subject to any disclaimer, the term of this patent is extended or adjusted under 35 U.S.C. 154(b) by 0 days.

(21) Appl. No.: 09/653,428

(22) Filed: Aug. 31, 2000

Related U.S. Application Data (60) Provisional application No. 60/151,820, filed on Sep. 1, 1999.

(51) Int. Cl.[7] .................................................. A61F 2/44
(52) U.S. Cl. .................................. 623/17.16; 623/17.11
(58) Field of Search ........................... 623/16.11, 17.11, 623/17.12, 17.13, 17.14, 17.15, 17.16, 17.17

(56) References Cited

U.S. PATENT DOCUMENTS

| | | | | |
|---|---|---|---|---|
| 5,094,618 A | * | 3/1992 | Sullivan | 433/173 |
| 5,390,693 A | | 2/1995 | Pisharodi | 128/898 |
| 5,393,036 A | | 2/1995 | Sheridan | 254/100 |
| 5,489,307 A | | 2/1996 | Kuslich et al. | 623/17 |
| 5,569,246 A | | 10/1996 | Ojima et al. | 606/61 |
| 5,593,409 A | | 1/1997 | Michelson | 606/61 |
| 5,609,635 A | | 3/1997 | Michelson | 623/17 |
| 5,665,122 A | | 9/1997 | Kambin | 623/17 |
| 5,693,100 A | | 12/1997 | Pisharodi | 623/17 |
| 5,700,291 A | | 12/1997 | Kuslich et al. | 623/17 |
| D392,387 S | | 3/1998 | Michelson | D24/155 |
| 5,766,010 A | * | 6/1998 | Uemura | 433/173 |
| 6,102,948 A | * | 8/2000 | Brosnahan, III | 623/17.16 |
| 6,273,722 B1 | * | 8/2001 | Phillips | 433/173 |

OTHER PUBLICATIONS

Technology Strategies: "Reconnecting With The Spinal Market" Facing a stagnant joint implant business, orthopedic companies are rediscovering the spinal market through new devices called interbody fusion cages. Stephen Levin Windhover Information Inc. (Start–up Apr. 1998).

* cited by examiner

*Primary Examiner*—Corrine McDermott
*Assistant Examiner*—Hieu Phan
(74) *Attorney, Agent, or Firm*—Oppenheimer Wolff & Donnelly LLP; Claude A. S. Hamrick (57) ABSTRACT

A spinal fusion implant device is provided for insertion into a generally cylindrical bore formed between adjacent vertebrae. The device includes: a shaft having a longitudinal central axis; and a plurality of projections extending radially from the shaft and terminating in a surface, each of the projections being oriented to form a thread like segment for engaging the internal surface of the cylindrical bore to advance the device axially into the bore upon rotation of the device about the longitudinal axis. In an embodiment, each of the projections includes an elongated member terminating in a surface including at least one rib adapted to form a thread like segment for engaging the internal surface of the bore. The elongated member further includes a bulbous head forming the surface at a distal end of the elongated member.

21 Claims, 5 Drawing Sheets

INTERVERTEBRAL SPACER IMPLANT

CROSS REFERENCE TO RELATED APPLICATIONS

Reference is made to and priority claimed from U.S. provisional application Ser. No. 60/151,820, filed Sep. 1, 1999, entitled "Intervertebral Spacer Implant", the disclosure of which is hereby incorporated in its entirety.

BACKGROUND OF THE INVENTION

1. Field of the Invention

The present invention relates generally to spinal fusion surgery apparatus. More specifically, the present invention relates to an interbody spinal fusion implant device adapted for insertion between opposing vertebrae to maintain separation thereof during the fusion process.

2. Description of the Prior Art

Spinal fusion surgery is often undertaken in treatment of pain associated with degenerative spinal disc disease and segmental instability of the spine. An intervertebral disc, which separates adjacent vertebrae, is comprised of a gel-filled nucleus encased by 18 rings of ligaments forming an exterior annulus. The most common type of disc failure occurs when the exterior annulus of the disc ruptures. A degenerated disc can result in spinal instability manifested as excessive movement of adjacent vertebrae which causes irritation of nerves resulting in back and leg pain. The object of spinal fusion surgery is to meld separate adjacent vertebrae into a single rigid bony mass in order to restore stability to the spine.

Spinal fusion surgical procedures generally include instrumented and non-instrumented fusion procedures. Non-instrumented fusion includes placing fusion promoting material between adjacent vertebrae to form shims in the corresponding intervertebral spaces to facilitate a calcification response by the body which effectively fuses the bony vertebral bodies together. The fusion promoting material may include bone plugs and bone chips harvested from the patient, and other osteo-inductive/conductive materials. Non-instrumented fusion techniques are implemented without installing any hardware to the spine to provide added rigidity, or intervertebral spacing.

Instrumented fusion procedures include the implanting of hardware such as intervertebral spacers, metal plates, pedicle screws, and rods for fastening the vertebrae together to provide rigidity and intervertebral spacing. Instrumented fusion procedures traditionally involve using a posterior approach that requires forming a large incision in the patients back, and stripping large muscles of the lower back away from the spine to allow access to the degenerated disc. A frequently used variation on posterior fusion is called a 360 degree procedure in which the spine is initially accessed using an anterior approach through a smaller incision in the patients abdomen, and subsequently accessed via another small incision in the patients back to insert instrumentation.

A stand-alone implant is a type of hardware commonly used in accordance with instrumented spinal fusion surgery wherein no additional instrumentation, such as hook and rod systems, is used to facilitate the spinal fusion. Stand-alone implants are inserted into a bore formed between adjacent vertebrae. A commonly used example of a stand-alone spinal fusion implant device is an interbody fusion cage.

Conventional interbody fusion cages typically include a hollow structure having an internal chamber for receiving fusion promoting material, the internal chamber being surrounded by external walls. The structure includes a plurality of openings formed in the exterior walls, the openings providing communication of the fusion promoting material between the internal chamber and the surfaces of the vertebrae between which the fusion cage is implanted. Communication of the fusion promoting material with the surfaces of the vertebrae induces calcification of the adjacent vertebrae for fusing the vertebrae together.

One of the most important advantages associated with the use of interbody fusion cages is the ability to perform spinal fusion surgery in a less traumatic way for the patient. Surgical techniques for implanting interbody fusion cages generally include the steps of: forming a bore between adjacent vertebrae; inserting a fusion cage into the bore; and inserting the fusion promoting material into the internal cavity. Currently, the most common surgical technique for implanting interbody fusion cages includes implanting two fusion cage devices at each level of the spine to provide balanced intervertebral spacing and support. In addition to the options of performing an implant procedure using traditional anterior and posterior techniques, interbody fusion cages allow surgeons the option of performing an implant procedure using laparoscopic techniques. Kuslich (U.S. Pat. No. 5,700,291, issued Dec. 23, 1997) describes one example of a laparoscopic spinal stabilization method wherein a cylindrical implant is passed through a cannula and inserted into a bore formed between opposing vertebrae.

Michelson (U.S. Pat. No. 5,593,409, issued Jan. 14, 1997) discloses an example of an interbody fusion cage device including a partially cylindrical structure formed by a wall surrounding an internal chamber for receiving the fusion promoting material. The wall has a plurality of openings passing therethrough providing communication between the internal chamber and surfaces of the vertebrae between which the device is implanted. The exterior surface of the device includes numerous ridges and channels for reducing the probability of dislodgment of the implant after insertion.

Kuslich et. al. (U.S. Pat. No. 5,489,307, issued Feb. 6, 1996) describes another cylindrical implant device which provides external threads facilitating screw-in fixing of the device between upper and lower vertebrae to provide support and correct vertical dimensions in the intervertebral space. Kuslich et. al. also describes tools and methods for insertion of implants. An insertion tool described by Kuslich et. al. includes a drill tube having serrated axially projecting teeth on the distal end. The serrated teeth of the tool dig into the bony exterior of the adjacent vertebrae, holding the tool secure and providing a guide for a reaming tool. The teeth of the tool do not cut deep, but merely provide a secure anchor for the tool on the exterior surface of the vertebrae. The ossicified bone within the cylinders is not exposed to the same compressing load from the weight of the open body, and therefore becomes very porous - no longer providing cephalo-caudad support and creating a weak interface with the bony matter surrounding the cage.

One common problem associated with conventional interbody fusion cages is that, despite being integrally formed using titanium, they are breakable. Conventional interbody fusion cages are prone to fracture due to vertical forces brought to bear across the hollow cage structure which is squeezed between the opposing vertebrae. A fractured cage no longer provides support and may be prone to movement, or migration.

Another problem associated with conventional interbody fusion cages is migration from the original implanted position. Conventional interbody fusion cage devices are rigid compared with the softer bone material of the vertebral bodies. This relative rigidity of the device may lead to disassociation from the surrounding fusion mass as a result of an inability to flex with the natural movement of the vertebrae and their interstices. Migration of the cage typically arises in response to mechanical manipulation occurring during normal physical activity wherein the more rigid titanium cage breaks free of it's bond with the surrounding bony material which is more flexible and compliant. Another factor which may contribute to migration is osteoporosis which is progressive and which leads to decreasing rigidity and strength of bones. This increases the potential for migration over time.

In an attempt to alleviate migration problems, some prior art devices include numerous ridges and channels formed on an exterior surface of the device for reducing the probability of dislodgment of the implant after insertion. Other devices include threaded walls which screw into bores formed between the vertebrae. However, migration remains a problem even in these types of devices.

Still another problem associated with conventional interbody fusion cages is that the wall surrounding the internal chamber substantially isolates the fusion promoting material inside the chamber from the normal stresses of weight bearing and physical activity. This is problematic because bone becomes weaker in the absence of loading. Calcium will be reabsorbed from the bone if it isn't loaded, and the bone will weaken. According to accepted bio-mechanical orthopedic theory, bone tissue which is not exposed to sufficient stress or which is not used effectively, does not harden to its full potential, and is prone to re-absorption. Due to the enclosed design of the cage, most of the fusion promoting material is effectively isolated from load bearing duty due to its enclosure within the walls of the internal chamber. Being thus insulated, the fusion promoting material is prevented from developing strength and hardness characteristics equal to that of the surrounding fusion mass.

Another problem associated with conventional interbody fusion cages is that they are difficult to retrieve, or remove. If a fusion cage requires removal, the calcification around the cage and the ingrowth of bony material makes retrieval very difficult.

What is needed is an interbody spinal fusion implant device which provides enhanced vertical (cephalo-caudad) and radial support between the vertebrae, increased strength characteristics, and increased resistance to compression fracture.

What is also needed is an interbody spinal fusion implant device capable of receiving fusion promoting material while installed between adjacent vertebrae, the structure providing an increased area of direct exposure of the fusion promoting material to the opposing vertebrae thereby subjecting the fusion material to increased load bearing duty and compression to promote strengthening of the fused material, and to achieve enhanced fusion of the vertebrae.

Further needed is an interbody spinal fusion implant device which is not prone to migration from its original implanted position.

SUMMARY OF THE INVENTION

It is therefore an object of the present invention to provide an improved interbody spinal fusion implant device adapted to be installed by surgical techniques including the laparoscopic approach, the anterior approach, or the posterior approach.

It is another object of the present invention to provide an interbody spinal fusion implant device which provides enhanced vertical (cephalo-caudad) and radial support between opposing vertebrae, increased strength characteristics, and increased resistance to compression fracture.

Yet another object of the present invention is to provide an interbody spinal fusion implant device having a structural framework capable of receiving fusion promoting material while installed between adjacent vertebrae, the framework providing an increased area of direct exposure of the fusion promoting material to the vertebrae thereby subjecting the material to increased compression to promote strengthening of the fused material, and to achieve enhanced fusion of the vertebrae.

A still further object of the present invention is to provide a spinal fusion implant device which is not prone to migration.

Briefly, a presently preferred embodiment of the present invention provides a spinal fusion implant device for insertion into a generally cylindrical bore formed between adjacent vertebrae, the device including: a shaft having a longitudinal central axis; and a plurality of projections extending radially from the shaft and terminating at a cylindrical locus concentric with the shaft. Interstitial spaces formed between the projections provide a receptacle for fusion promoting material subsequently injected thereinto. In one embodiment, each of the projections is shaped and oriented to form a thread like segment for engaging the internal surface of the cylindrical bore to advance the device axially into the bore upon rotation of the device about the longitudinal central axis of the shaft.

In one embodiment, each of the projections includes an elongated member terminating in a surface at its distal end including at least one rib adapted to form the thread like segment for engaging the internal surface of the bore. The elongated member further includes a bulbous head forming the surface at the distal end of the elongated member.

An important advantage of the present invention is that the projections provide enhanced vertical (cephalo-caudad) and radial support between the vertebrae.

Another advantage of the present invention is that the interstitial spaces formed between the projections provide a large amount of mechanical purchase on the surrounding fusion material and bone. This mechanical purchase inhibits migration of the device from its original implanted position.

An additional advantage of the present invention is that fusion promoting material inserted between the plurality of projections and the shaft is provided with a large area of direct contact with the adjacent vertebrae thereby subjecting the fusion promoting material to the normal stress of weight bearing thereby promoting strengthening of fused material, and achieving enhanced fusion of the vertebrae. The increased bone compression provides increased longevity of the fusion.

The foregoing and other objects, features, and advantages of the present invention will be apparent from the following detailed description of the preferred embodiment which makes reference to the several figures of the drawing.

DETAILED DESCRIPTION OF THE PREFERRED EMBODIMENTS

Figure 1A:
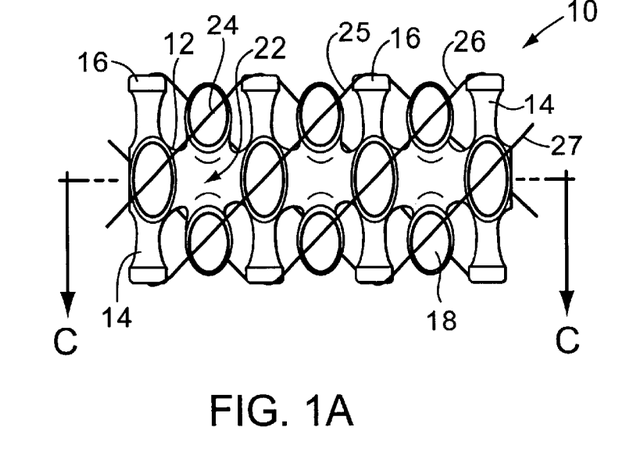
FIG. 1A is a side elevation illustrating an interbody implant device in accordance with a first embodiment of the present invention including a shaft, and a plurality of projections each extending radially from the shaft and having an enlarged head formed at its distal end.

Referring to the drawing, FIG. 1A shows a side elevation illustrating an interbody implant device at 10 in accordance with a first embodiment of the present invention including a longitudinal shaft 12, and a plurality of stub-like projections 14 extending radially from the shaft, each of the projections 14 having a biscuit-shaped, or domed cylindrical shaped, head 16 formed at its distal end, with each head 16 having a top surface 18. A framework of interstitial spaces 22 formed between the projections 14 provides a tortuous receptacle for receiving fusion promoting material following installation of the device 10 into a bore formed between adjacent vertebrae of a patient, as further explained below.

In the depicted embodiment, each of the radial projections 14 is formed by an integral cylindrical stud and cap having a shape somewhat like a nail head. In the depicted embodiment, the top surface 18 of each of the projections 14 is formed in a plane parallel to a plane that is tangent to the surface of the shaft 12 at the point of intersection of the projections 14 and the shaft 12.

In the illustrated embodiment, the shaft 12 is substantially cylindrical. However, in an alternative embodiment, the shaft might be somewhat frusto-conical or have a cross section that is circular, rectangular, hexagonal, octagonal, elliptical, or of any other suitable polygonal configuration. Also, in the preferred embodiment, the radially extending projections 14 are formed by cylindrical members. However, it is to be understood that any appropriate structure forming a rigid sturdy elongated member may be used to implement the radial projections 14.

In one embodiment, the device 10 is formed by drilling holes in the exterior surface of the shaft 12 and inserting the projections 14 into the holes. In an alternative embodiment, the shaft 12 and radial projections 14 may be formed in an integral relationship by casting, molding, machining, or using any other suitable manufacturing process. As further explained below, the implant device 10 is adapted for insertion into a cylindrical bore formed between adjacent vertebrae by surgical coring or drilling apparatus.

Figure 1B:
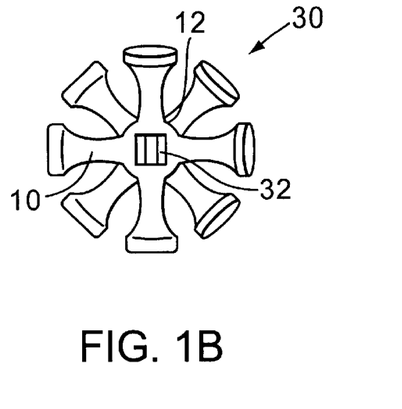
FIG. 1B is an end view of the implant device of FIG. 1A, showing a slotted recess formed in an end of the shaft for receiving an insertion/removal tool.

FIG. 1B shows an end view at 30 of the implant device 10 which further includes a slotted recess 32 formed in an end of the shaft 12 for receiving the end of an insertion/removal tool (not shown) for rotating the device 10 about the longitudinal axis of the shaft causing it to advance into a cylindrical bore formed between adjacent vertebrae. In alternative embodiments of the present invention, the implant device may include a recess or socket of any other appropriate shape formed therein for receiving or otherwise engaging an insertion tool at an end of the shaft 12.

By jointly considering the side and end views shown in FIGS. 1A and 1B it will be appreciated that as in the other embodiments to be discussed below, there are twenty eight projections 14 (although there could be more or less than twenty eight) extending radially relative to shaft 12 in groups of four, with each such group lying in one of seven planes transversely intersecting the axis of shaft 12. Furthermore, the projections of alternate groups are rotated 45 degrees about shaft 12 relative to the projections of the other groups of projections so that the distal end faces 15 of the heads 16 lie in one of four helical paths as depicted by the solid and dashed lines 24–27. As in the other embodiments, each head end face in effect forms a segments of one of four virtual helical threads wrapping around the device and serving as a means for advancing the device into position between vertebrae as explained below.

Figures 1C, 2:
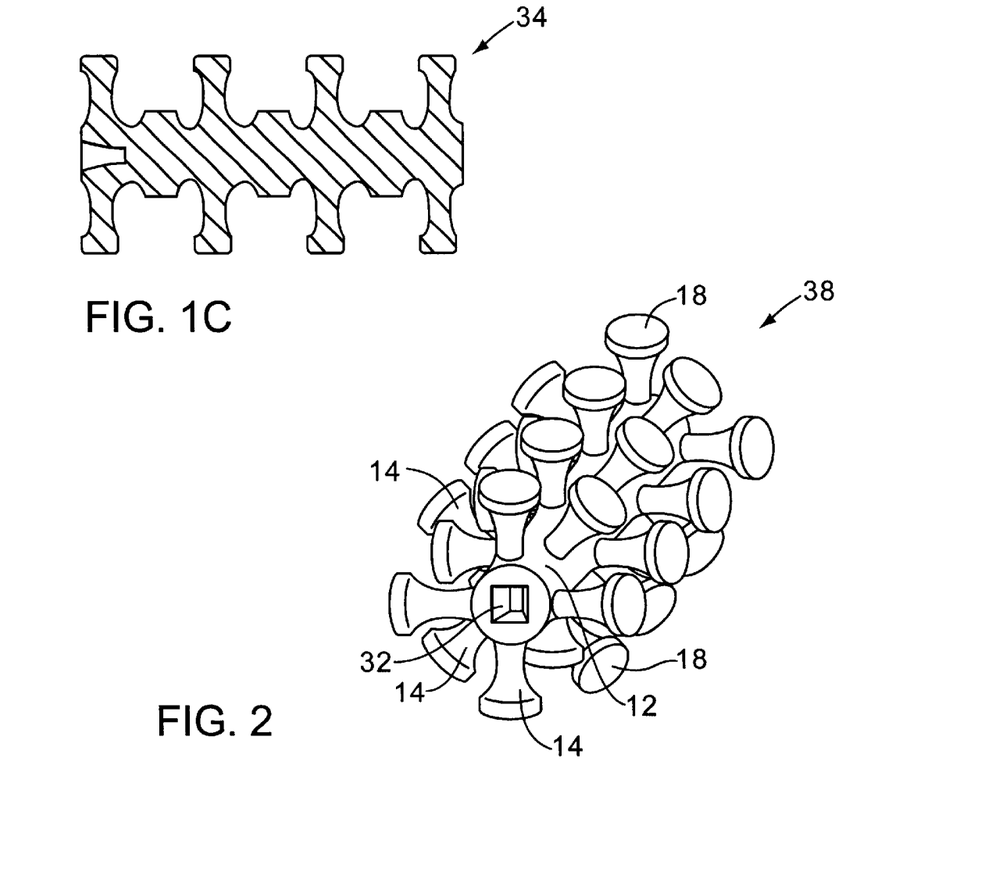
FIG. 1C is a cross sectional view of the implant device of FIG. 1A taken generally along the line C—C of FIG. 1A.
FIG. 2 is a perspective view of the interbody implant device of FIG. 1A.

FIG. 1C shows a cross sectional view at 34 of the implant device 10 (FIG. 1A) taken generally along the line C—C of FIG. 1A.

FIG. 2 shows a perspective view at 38 of the interbody implant device of FIG. 1A. In the depicted embodiment, the radial projections 14 are disposed along the shaft 12 in annular arrays. In alternative embodiments, the radial projections 14 may be disposed along the shaft 12 in a spiral array and in a random array.

Figure 3:
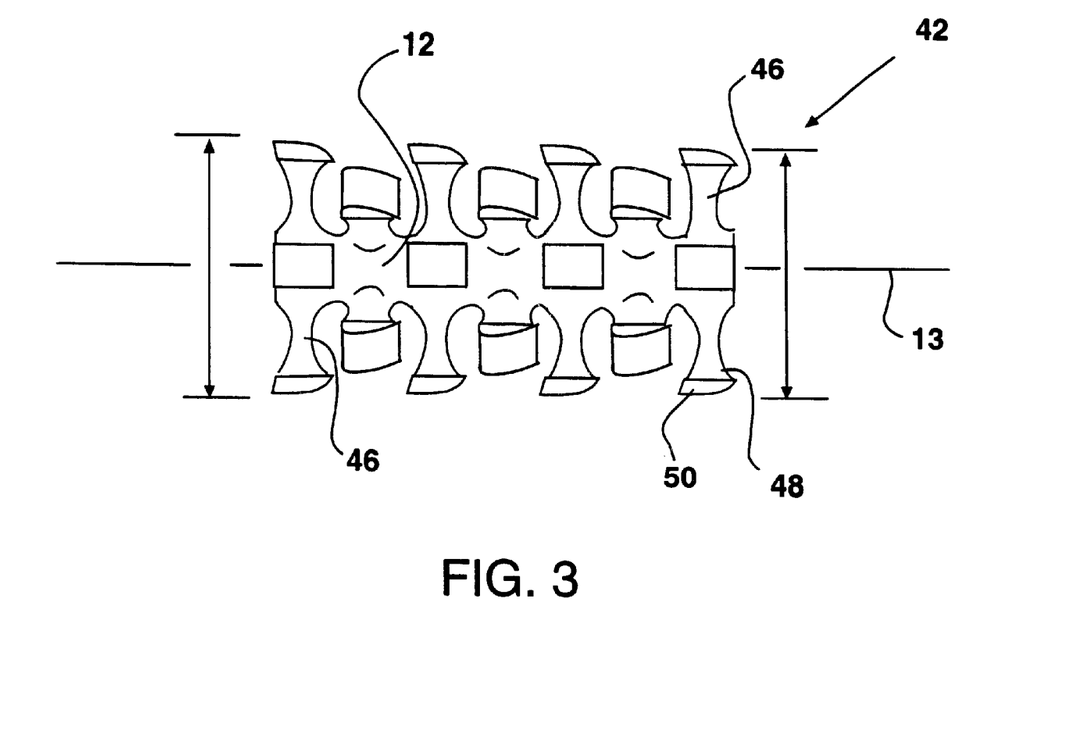
FIG. 3 is a side elevation view of an implant device in accordance with a second embodiment of the present invention wherein each of the heads is generally wedge-shaped and oriented so that the device may be easily inserted into a bore formed between opposing vertebrae.

FIG. 3 shows a side elevation view illustrating an implant device at 42 in accordance with a second embodiment of the present invention. The device 42 includes a longitudinal shaft 12, and a plurality of stub-like projections 46 extending radially from the shaft, each of the projections 46 having a generally wedge-shaped head 48 formed at its distal end, each head 48 having a curved top surface 50. The wedge-shaped head 48 has a generally tear-drop shaped cross section. Each of the heads 48 has a longitudinal axis extending parallel to the longitudinal axis 13 of the shaft so that the device may be easily inserted into a bore formed between opposing vertebrae. Each of the heads 48 has a leading section which is narrower than a trailing section, the leading section to precede the trailing section in the direction of insertion of the device into the bore. A framework of interstitial spaces formed between the projections 46 provides a tortuous receptacle for receiving fusion promoting material following installation of the device 10 into a bore formed between adjacent vertebrae of a patient, as further explained below.

Figure 4:
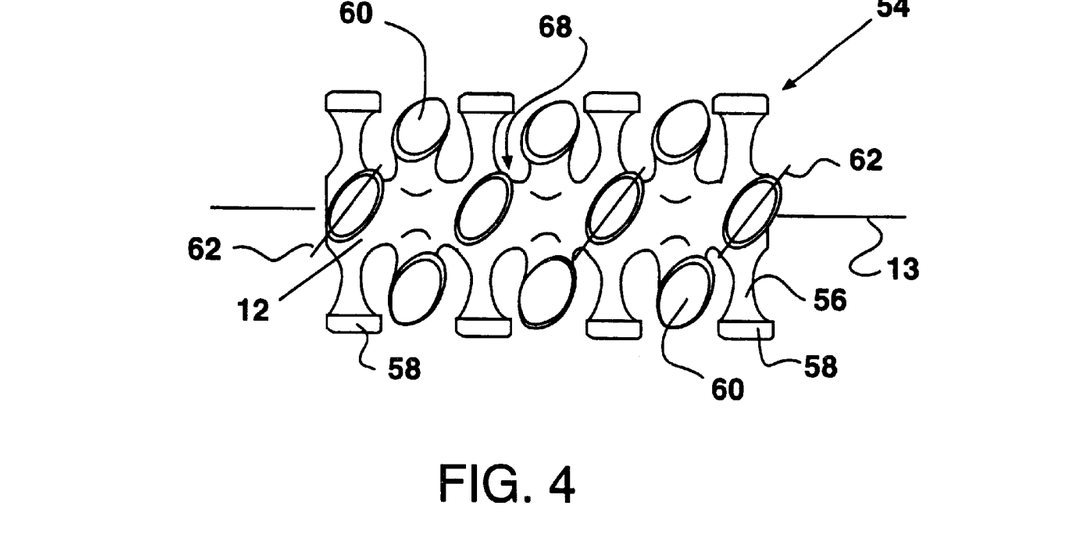
FIG. 4 is a side elevation view of an implant device in accordance with a third embodiment of the present invention wherein each of the heads is formed by an elongated disc-shaped head having a longitudinal axis extending at an angle relative to a transverse plane that is normal to the longitudinal axis of the shaft such that the longitudinal axis of each head forms a segment of one or more virtual helical "threads" wrapped about the device.

FIG. 4 shows a side elevation view illustrating an implant device at 54 in accordance with a third embodiment of the present invention. The device 54 includes a longitudinal shaft 12, and a plurality of stub-like projections 56 extending radially from the shaft, each of the projections 56 having an elongated disc-shaped head 58 formed at its distal end, each head 58 having an oval-shaped top surface 60. Each of the heads 58 has a longitudinal axis 62 extending at an angle relative to a transverse plane that is normal to the longitudinal axis 13 of the shaft such that the longitudinal axis 62 of each head 58 forms a segment of one or more virtual helical "threads" wrapped about the device. A framework of interstitial spaces 68 formed between the projections 56 provides a tortuous receptacle for receiving fusion promoting material following installation of the device 10 into a bore formed between adjacent vertebrae of a patient, as further explained below.

Figure 5:
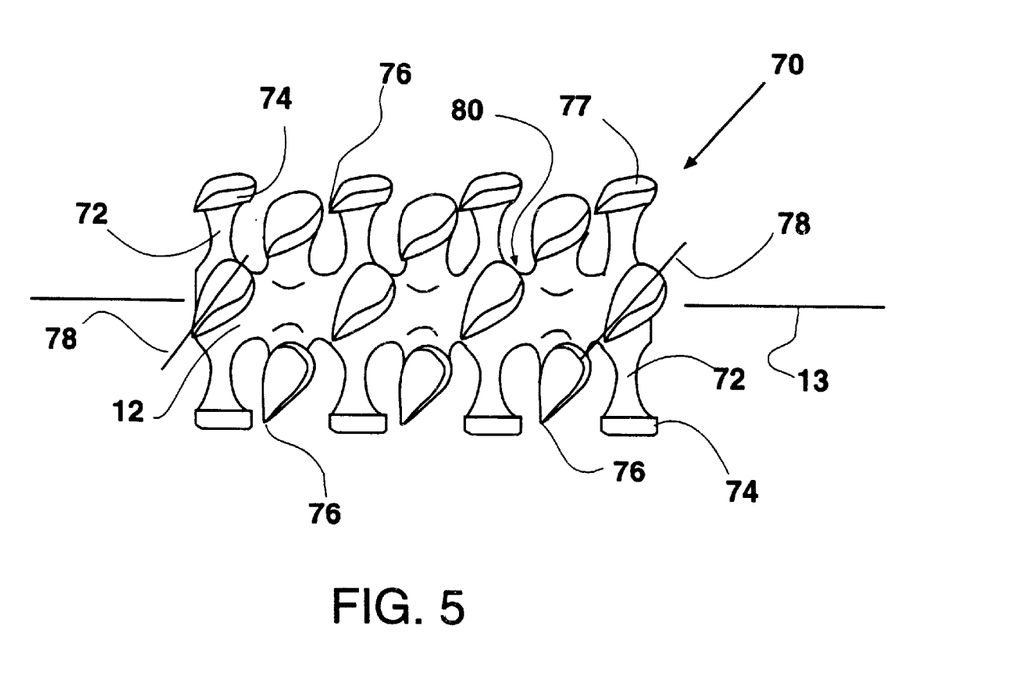
FIG. 5 is a side elevation view of an implant device in accordance with a fourth embodiment of the present invention similar to the device of FIG. 5 wherein each of the heads has a pointed leading end oriented in a direction along the virtual helical thread.

FIG. 5 shows a side elevation view of an implant device at 70 in accordance with a fourth embodiment of the present invention. The device 70 includes a longitudinal shaft 12, and a plurality of stub-like projections 72 each extending radially from the shaft. Each of the projections 72 has an elongated generally tear drop-shaped head 74 formed at its distal end, each head 74 having a tear drop-shaped top surface 60. Each of the heads 74 has a pointed front end, or leading end, 76 oriented along an axis 78 extending at an angle relative to a transverse plane that is normal to the longitudinal axis 13 of the shaft such that the pointed leading end 76 of each head is oriented along one more virtual helical "threads" wrapped about the device 70. A framework of interstitial spaces 80 formed between the projections 72 provides a tortuous receptacle for receiving fusion promoting material following installation of the device 10 into a bore formed between adjacent vertebrae of a patient, as further explained below.

FIG. 5 shows a side elevation view of an implant device at 70 in accordance with a third embodiment of the present invention. The device 70 includes a longitudinal shaft 12, and a plurality of stub-like projections 72 each extending radially from the shaft. Each of the projections 72 has an elongated generally tear drop-shaped head 74 formed at its distal end, each head 74 having a tear drop-shaped top surface 60. Each of the heads 74 has a pointed front end, or leading end, 76 oriented along an axis 78 extending at an angle relative to a transverse plane that is normal to the longitudinal axis 13 of the shaft such that the pointed leading end 76 of each head is oriented along one more virtual helical "threads" wrapped about the device 70. A framework of interstitial spaces 80 formed between the projections 72 provides a tortuous receptacle for receiving fusion promoting material following installation of the device 10 into a bore formed between adjacent vertebrae of a patient, as further explained below.

The pointed leading ends 76 of the heads 74 provide means for engaging the internal surface of a bore formed between adjacent vertebrae of a patient to advance the device 70 axially into the bore upon rotation of the device about its longitudinal axis. As depicted, each of the heads 74 is tapered. Consequently, the front or leading ends 76 of each of the heads 74 is narrower than a trailing edge 77 thereof. The leading end of each of the blades precedes the trailing end in the advancing rotational direction of the interbody implant device about the longitudinal axis of the shaft. In this embodiment, the pointed leading ends 76 of the heads 74 form a discontinuous helical threading around the shaft 12 at a generally fixed radial distance from the central longitudinal axis 13 of the shaft 12.

Figure 6:
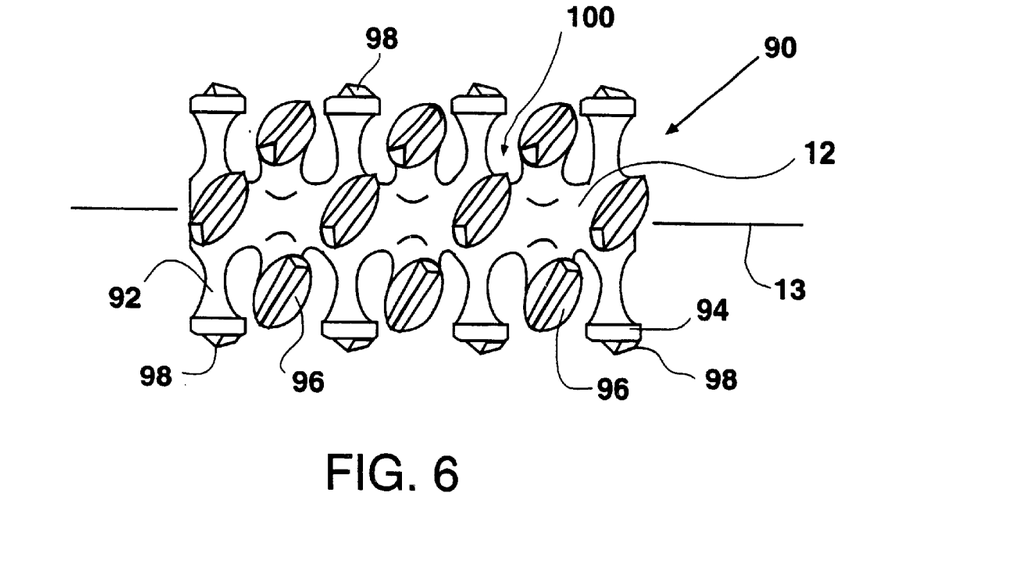
FIG. 6 is a side elevation view of an implant device in accordance with a fifth embodiment of the present invention wherein each of the heads has rib forming a thread like segment protruding from its top surface, each rib forming a segment of one or more virtual helical "threads" wrapped about the device.

FIG. 6 shows a side elevation view illustrating an implant device at 90 in accordance with a fifth embodiment of the present invention. The device 90 includes a longitudinal shaft 12, and a plurality of stub-like projections 92 extending radially from the shaft, each of the projections 92 having an elongated disc-shaped head 94 formed at its distal end, each head 94 having an oval-shaped top surface 96. Each of the heads 94 has at least one rib 98 forming a thread like segment protruding from its top surface 96. Each of the ribs 98 has a length which extends at an angle relative to a transverse plane which is normal to the longitudinal axis 13 of the shaft 12 such that each rib forms a segment of one or more virtual helical "threads" wrapped about the device.

A framework of interstitial spaces 100 formed between the projections 92 provides a tortuous receptacle for receiving fusion promoting material following installation of the device 90 into a bore formed between adjacent vertebrae of a patient, as further explained below. The ribs 98 provide means for engaging the internal surface of a bore formed between adjacent vertebrae of a patient to advance the device 90 axially into the bore upon rotation of the device about its longitudinal axis. In this embodiment, the ribs 98 form a discontinuous helical threading around the shaft 12 at a generally fixed radial distance from the central longitudinal axis 13 of the shaft 12.

In accordance with one aspect of the present invention, the segmented virtual helical threading formed by the ribs 98 of the device 90 has a varying pitch wherein the thread pitch increases or decreases gradually from one end of the device 90 to another along the longitudinal axis 13 of the device. In one embodiment, the thread pitch increases along the longitudinal axis 13 from a leading end of the device 90, which is to be inserted into the bore first, toward a trailing end of the device which follows the leading end into the bore so that the thread pitch at the trailing end is finer than the thread pitch at the leading end. The varying thread pitch provides for enhanced rotational stability, and a more stable locking mechanism for the device 90 after it has been inserted into the bore formed between adjacent vertebrae of a patient. Note that in this embodiment, the varying pitch may cause a stripping effect as the device 90 is tapped into the bore in the bony material of the vertebrae which is more or less compliant. The stripping effect arises as initially formed tracking (initially formed around the periphery of the bore by coarser pitched ribs 98 disposed along the leading portion of the device 90) is stripped by finer pitched ribs 98 disposed along the trailing portion of the device 90. Note further that the stripped portions of the bone will heal.

In accordance with the present invention, the segmented virtual helical threading formed by the heads of each of the devices 54 (FIG. 4), 70 (FIG. 5) may also have a varying pitch to achieve enhanced rotational stability as described for the device 90.

Surgical Technique

An interbody implant device according to the present invention may be installed in accordance with a variety of surgical procedures using anterior, posterior, or laparoscopic approach techniques or any combination thereof. In a posterior approach, a surgeon seeks access to the spine through the back of the patient. Using an anterior approach, the surgeon seeks access to the spine through the abdomen of a patient. The anterior approach can be done through open surgery or through laparoscopic surgery. The present invention can be used in an anterior approach for both laparoscopic or non-laparoscopic procedures. Once the surgeon has identified two vertebrae which are to be fused together, he identifies an implant device 10 of a desired size and determines the desired amount of distraction to be required between the vertebrae before placement of the implant. In selecting the implant size, the surgeon should ensure that the device will not extend beyond the lateral borders of the intervertebral disc.

In accordance with the posterior technique, a patient is placed on the operating table in either a prone or kneeling-sitting position. At the discretion of the surgeon, the spine is flexed slightly. Anesthesia is administered. Exposure of the intervertebral disc is obtained through any suitable technique well-known in the art. The facet of the vertebrae is removed in as limited amount as possible to permit insertion of the instruments and the implants. Preferably, bone dissected from the lamina, facets and spinous process are preserved for later use as bone graft material.

Figure 7:
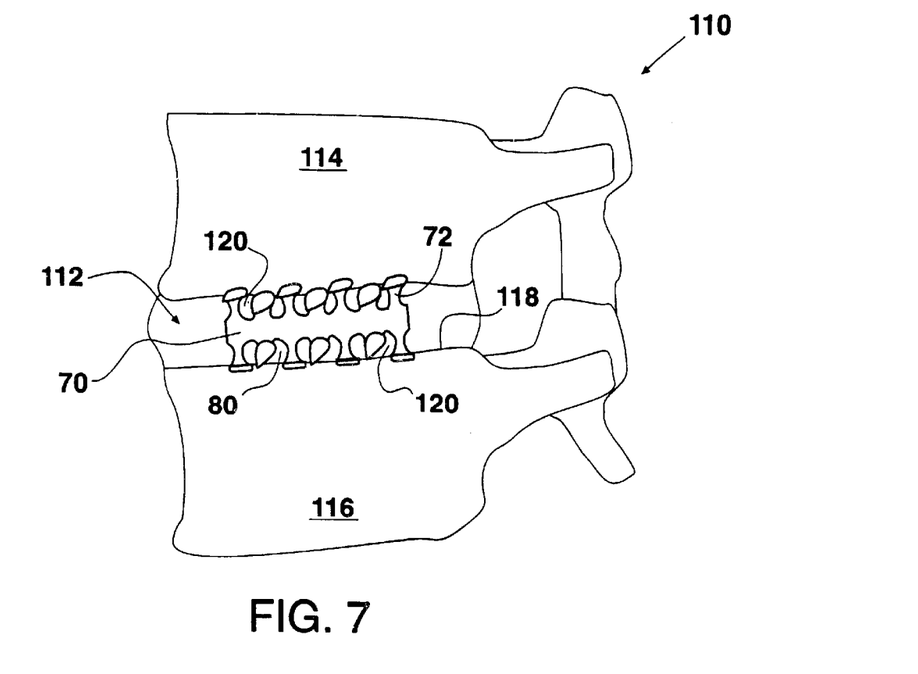
FIG. 7 is a cross sectional view taken longitudinal along the longitudinal axis of the implant device of FIG. 5 inserted into a bore formed between opposing vertebrae.

FIG. 7 shows a cross sectional side view at 110 of the implant device 70 inserted into a bore 112 formed between a first vertebra 114, and a second vertebra 116 which is adjacent to the first vertebra, the bore 112 having an interior surface 118. Fusion promoting material 120 is inserted into the framework of interstitial spaces 80 formed between the projections 72. The fusion promoting material 120 may include bone plugs and bone chips harvested from the patient, and other osteo-inductive/conductive materials.

As mentioned above, the pointed leading ends 76 of the heads 74 provide means for engaging the interior surface 118 of the cylindrical bore 112 to advance the device 70 axially into the bore upon rotation of the device in a particular direction about the longitudinal axis of the shaft 12. The device 70 may be rotated using a torquing tool which fits into a slotted recess similar to the recess 32 (FIG. 2) in the cylinder 12. Engagement of the pointed leading ends 76 of the heads 74 with the vertebrae 114 and 116 and the subsequent fusion of the injected material provides an effective anchoring of the device 70 between the vertebrae to prevent the device 70 from migrating from its original implanted position.

The bore 112 may be formed in accordance with various well known surgical techniques. Because vertebrae size and disc cavity dimensions will vary between patients, the device 70 is provided in a range of sizes having varying diameters and axial lengths. In order to allow the pointed leading ends 76 of the heads 74 to tap into the interior wall 118 of the bore 112, the bore is formed to have a diameter slightly smaller than the diameter of the device 70. As mentioned, the device 70 may be inserted into the bore 112 in accordance with surgical techniques including anterior, posterior, and laparoscopic approaches.

The framework of interstitial spaces 80 provided by the device 70 optimizes exposure of the fusion promoting material to compression forces transmitted by the adjacent vertebrae 114 and 116 as a result of normal weight bearing and physical activity. By allowing for a substantial portion of the total vertical and radial stresses exerted by the vertebrae 114 and 116 to be exerted upon the fusion promoting material 120, use of the device 70 promotes calcification and strength of the fused material.

The projections 72 of the device 70, which provide vertical (cephalo-caudad) and radial support between the vertebrae 114 and 116, provide enhanced strength characteristics over conventional interbody fusion cages. The strength characteristics of the projections 72 of the device provide a resistance to compression fracture as compression forces are exerted upon the implanted device. The projections 72, having heads 74 formed at the distal end thereof, also provide a large mechanical purchase to prevent the dislodgment or migration of the device 70 from its original position, implanted into the bore 112.

Figure 8:
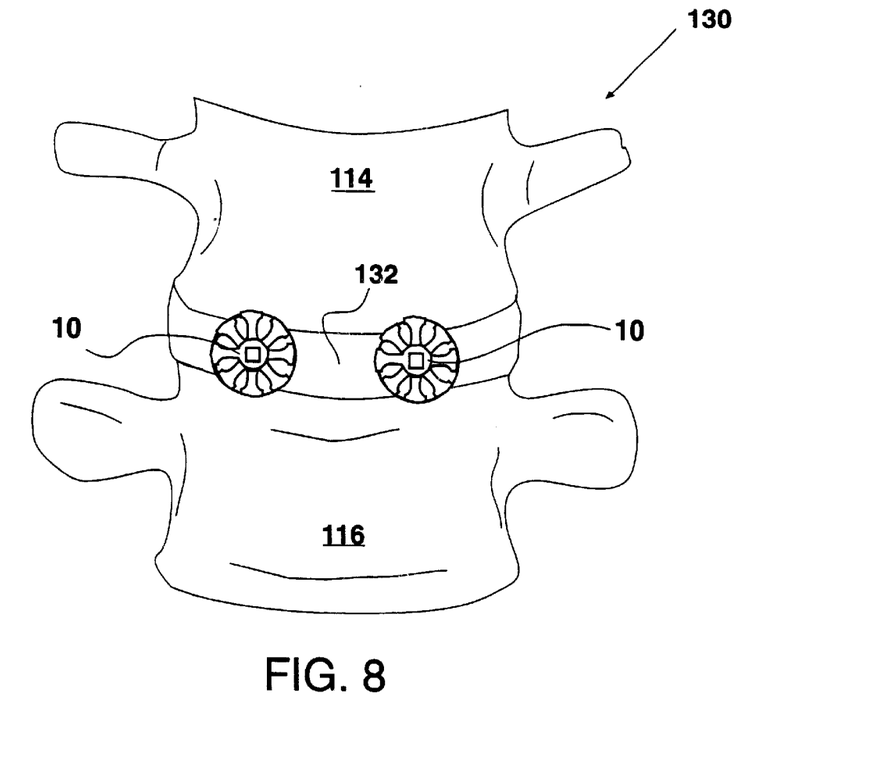
FIG. 8 is an anterior view illustrating two of the implant devices of FIG. 1A inserted into a pair of bores formed side by side and extending across a disk space between opposing vertebrae.

FIG. 8 shows an anterior view at 130 illustrating two of the implant devices 10 according to the present invention inserted side-by-side across a disk space 132 between upper and lower vertebrae 114 and 16. It is desirable to place two implant devices within the transverse width of the spine, between opposing vertebrae, in order to provide a more stable construct. The two implant procedure is preferable over the single implant procedure because the two implants provide a more stable construct. In a two implant procedure, bores are formed on opposite sides of the vertebrae to receive the implants.

Figure 9:
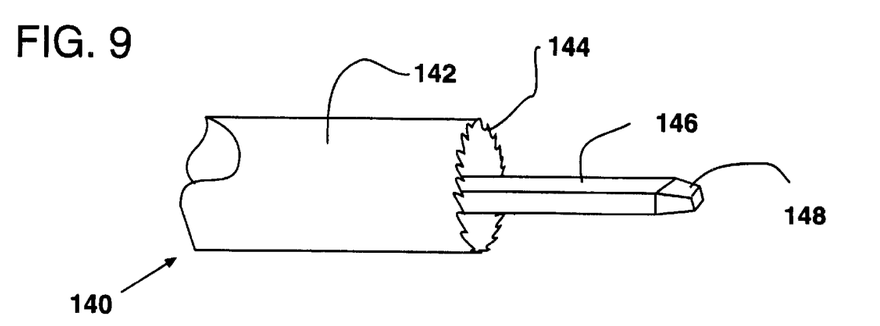
FIG. 9 is a perspective view of an implant removal tool including a tube having a serrated end, and a blade-tipped rod for engaging the slotted recess depicted in FIG. 1B in order to rotate the device.

FIG. 9 shows a perspective view of an implant removal tool at 140 including a hollow tube 142 having a serrated end 144; and a solid insertion/removal rod 146 disposed inside the tube 142 and having a concentric relationship with the tube. In the depicted embodiment, the rod 146 includes a head 148 for engaging the slotted recess 32 (FIG. 2) formed in the end of the shaft 12 (FIG. 2).

The tube 142 is formed to have an inner diameter which is slightly larger than the outer diameter of the implant device to be removed. The rod 146 may be coupled with a rotating means (not shown) for rotating the rod 146 about its longitudinal axis. The tube 142 may also be connected to a rotating means (not shown) for facilitating rotation of the tube about its longitudinal axis. The rod 146 and tube 142 may be rotated independently of the rotation of each other.

Figure 10:
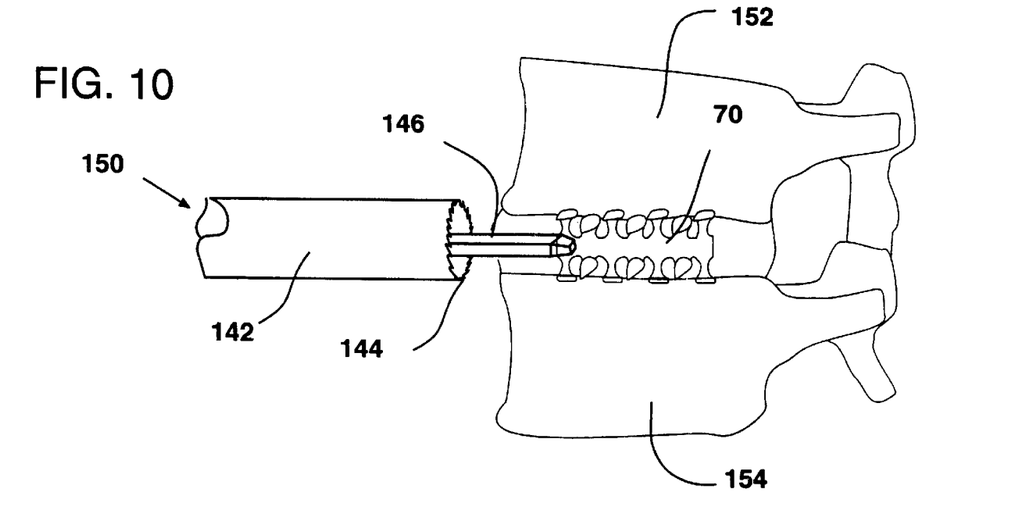
FIGS. 10 and 11 are cross sectional side views of the tool of FIG. 9 being applied to remove a device according to the present invention which is implanted between opposing vertebrae that has been fused together.

FIG. 10 shows a cross sectional side view at 150 showing the implant removal tool 140 being used to remove the device 10 which is implanted between a pair of fused vertebral bodies 152 and 154. The tube 142 has an inner diameter which is slightly larger than the outer diameter of the implant device 10.

The head 148 of the rod 146 is inserted into the slotted recess (not shown) of the shaft 12 (FIG. 2) of the implant device 10. The tube 142 is then rotated as the serrated end 144 of the tube is forced against the bony material of the fused vertebral bodies 152 and 154. As the tube 142 is rotated, the serrated end 144 of the tube cuts into the bony material of the fused vertebral bodies and the tube is advanced over the device 10.

Figure 11:
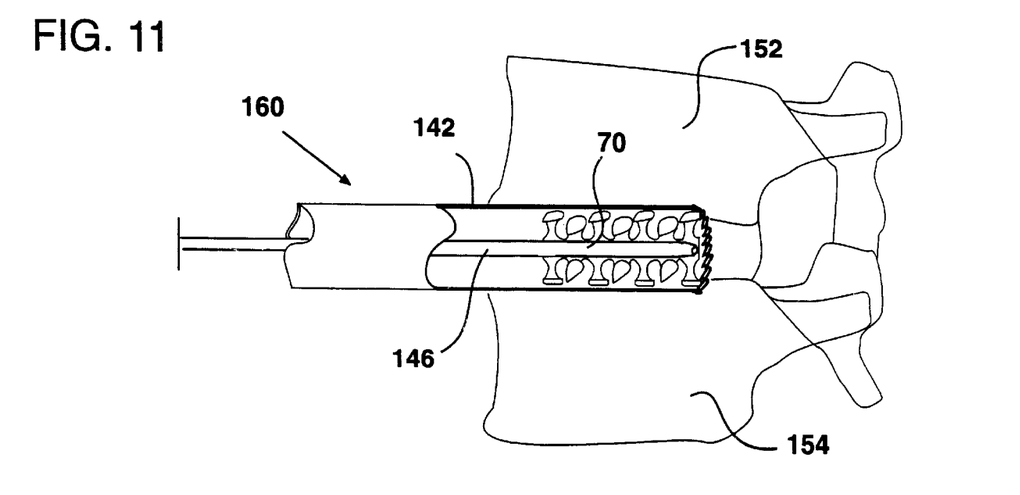

FIG. 11 shows a cross sectional view at 160 showing the implant removal tool 140 being used to remove the device 10 which is implanted between the fused vertebral bodies 152 and 154, wherein the tube 142 is advanced into the bony material of the fused vertebral bodies 152 and 154 to a depth equal to the length of the device 10. At this point, the device 10 may be dislodged by rotating the rod 146 in a rotational direction opposite the direction of rotation used to insert the device 10 as described above.

Although the present invention has been particularly shown and described above with reference to a specific embodiment, it is anticipated that alterations and modifications thereof will no doubt become apparent to those skilled in the art. It is therefore intended that the following claims be interpreted as covering all such alterations and modifications as fall within the true spirit and scope of the invention.

What is claimed is:

1. A spinal fusion implant device for insertion into a bore formed between adjacent vertebrae, said device comprising:
   a shaft having a longitudinal axis; and
   a plurality of projections each extending radially from said shaft and terminating in a corresponding projection surface, said projections being arranged in groups of at least four projections radially extending from said shaft in planes transverse to and axially separated along the length of said shaft, each said projection having an elongated shank portion with a first transverse cross sectional area, and a head portion with a second transverse cross sectional area larger than said first cross sectional area, said device having interstitial spaces forming a tortuous receptacle between said projections for receiving fusion promoting material.

2. A spinal fusion implant device as recited in claim 1 wherein each of said projection surfaces is shaped and oriented to form a thread like segment for engaging the internal surface of the bore to advance said device axially into the bore upon rotation of said device in a particular rotational direction about said axis.

3. A spinal fusion implant device as recited in claim 2 wherein:
   said projections comprise a plurality of elongated members terminating in said corresponding projection surfaces; and
   each of said projection surfaces includes at least one rib protruding therefrom and adapted to form one of said thread like segments.

4. A spinal fusion implant device as recited in claim 3 wherein each of said elongated members is formed by a substantially cylindrical member having a substantially domed cylindrical shaped head formed at a distal end thereof.

5. A spinal fusion implant device as recited in claim 3 wherein each of said ribs extends at an angle relative to a transverse plane which is normal to said longitudinal axis.

6. A spinal fusion implant device as recited in claim 5 wherein said ribs form a discontinuous helical threading along a cylindrical locus concentric with said shaft.

7. A spinal fusion implant device as recited in claim 2 wherein said projection surfaces forming thread like segments are configured to form a discontinuous helical threading having a varying pitch.

8. A spinal fusion implant device as recited in claim 7 wherein said discontinuous helical threading increases along said longitudinal axis of said shaft from a leading end of the device that is to be inserted into the bore first, toward a trailing end of the device that is to follow said leading end into the bore.

9. A spinal fusion implant device as recited in claim 1 wherein said projections and said shaft are formed in an integral relationship.

10. A spinal fusion implant device as recited in claim 1 wherein one end of said shaft has means formed thereon for engaging a rotary driver means for rotating said device in said particular rotational direction to advance said device axially into the bore, and for rotating said device in a rotational direction opposite said particular rotational direction to retrieve said device from said bore.

11. A spinal fusion implant device as recited in claim 1 wherein:
   said projections comprise a plurality of elongated members terminating in said corresponding projection surfaces; and
   each of said projection surfaces is formed by an elongated disc-shaped head formed at a distal end of the corresponding projection, each said head having a longitudinal axis extending at an angle relative to a transverse plane that is normal to the longitudinal axis of said shaft, said heads for engaging the internal surface of the bore to advance said device axially into the bore upon rotation of said device in a particular rotational direction about said axis.

12. A spinal fusion implant device as recited in claim 1 wherein:
   said projections comprise a plurality of elongated members terminating in said corresponding projection surfaces; and
   each of said projection surfaces is formed by an elongated head formed at a distal end of the corresponding projection, each said head having a pointed leading end oriented at an angle relative to a transverse plane that is normal to said longitudinal axis of said shaft, said heads for engaging the internal surface of the bore to advance said device axially into the bore upon rotation of said device in a particular rotational direction about said axis.

13. A spinal fusion implant device as recited in claim 1 wherein:
   said projections comprise a plurality of elongated members terminating in said corresponding projection surfaces; and
   each of said projection surfaces is formed by a generally wedge-shaped head formed at a distal end of the corresponding projection, each said head having a leading section which is narrower than a trailing section, wherein the leading section is to precede the trailing section in a direction of insertion of the device into a bore formed between opposing vertebrae.

14. A spinal fusion implant device for insertion into a bore formed between adjacent vertebrae, said device comprising:
   a shaft having a longitudinal axis;
   a plurality of elongated members each having a longitudinal axis extending radially from said shaft, with each said member terminating in a corresponding distal end surface adapted to form a thread like segment for engaging the internal surface of the bore to advance said device axially into the bore upon rotation of said device in a particular rotational direction about the axis of said shaft, said device having interstitial spaces between said elongated members forming a tortuous receptacle for receiving fusion promoting material.

15. A spinal fusion implant device as recited in claim 14 wherein each of said elongated members is formed by a substantially cylindrical member having a substantially domed cylindrical shaped head formed at the distal end thereof.

16. A spinal fusion implant device as recited in claim 14 wherein each of said corresponding surfaces have at least one rib protruding therefrom with each said rib having a length extending at an angle relative to a transverse plane which is normal to said longitudinal axis.

17. A spinal fusion implant device as recited in claim 16 wherein said ribs form a discontinuous helical threading along a cylindrical locus concentric with said shaft.

18. A spinal fusion implant device as recited in claim 14 wherein said projections and said shaft are formed in an integral relationship.

19. A spinal fusion implant device as recited in claim 14 wherein one end of said shaft has means formed thereon for engaging a rotary driver means for rotating said device in said particular rotational direction to advance said device axially into the bore, and for rotating said device in a rotational direction opposite said particular rotational direction to retrieve said device from said bore.

20. A spinal fusion implant device as recited in claim 14 wherein said projection surfaces forming thread like segments are configured to form a discontinuous helical threading having a varying pitch.

21. A spinal fusion implant device as recited in claim 20 wherein said discontinuous helical threading increases along said longitudinal axis of said shaft from a leading end of the device that is to be inserted into the bore first, toward a trailing end of the device that is to follow said leading end into the bore.

* * * * *